(12) United States Patent
Haynes, Jr.

(10) Patent No.: US 7,026,344 B2
(45) Date of Patent: Apr. 11, 2006

(54) TREATING SICKLE CELL DISEASE

(75) Inventor: Johnson Haynes, Jr., Mobile, AL (US)

(73) Assignee: South Alabama Medical Science Foundation, Mobile, AL (US)

( * ) Notice: Subject to any disclaimer, the term of this patent is extended or adjusted under 35 U.S.C. 154(b) by 350 days.

(21) Appl. No.: 10/344,727

(22) PCT Filed: Aug. 15, 2001

(86) PCT No.: PCT/US01/25379

§ 371 (c)(1),
(2), (4) Date: May 20, 2003

(87) PCT Pub. No.: WO02/13818

PCT Pub. Date: Feb. 21, 2002

(65) Prior Publication Data

US 2005/0101659 A1    May 12, 2005

Related U.S. Application Data

(60) Provisional application No. 60/225,605, filed on Aug. 15, 2000.

(51) Int. Cl.
*A61K 31/44* (2006.01)
*A61K 31/41* (2006.01)

(52) U.S. Cl. .................... 514/381; 514/415; 514/443

(58) Field of Classification Search ................ 514/381, 514/443, 415
See application file for complete search history.

(56) References Cited

U.S. PATENT DOCUMENTS

| 4,873,259 A | 10/1989 | Summers, Jr. et al. |
| 5,629,337 A | 5/1997 | Gray |
| 5,817,684 A | 10/1998 | Fleisch et al. |

FOREIGN PATENT DOCUMENTS

WO    WO 96/20936 A1 * 7/1996

OTHER PUBLICATIONS

"The 5-Lipoxygenase Inhibitory Activity of Zileuton in In Vitro and In Vivo Models of Antigen-Induced Airway Anaphylaxis", Malo et al., Pulmonary Pharmacology, abstract, vol. 7, Issue 2, Apr. 1994, pp. 73-79.*
"Zileuton: A Potential New Treatment Approach For Acute Chest Syndrome", Dixon et al., Bloood, abstract, Nov. 2000, vol. 96, No. 11, Par 1, pp. 10a.*
"The Effect of 5-Lipoxygenase Inhibition by Zileuton on Platelet-Activating-Factor-Induced Pulmonary Abnormalties in Mild Asthma", Gomez et al, Am J Resp Crit Care Med 1998, vol. 157, pp. 1559-1564.*
"Lipoxygenase Inhibitors as Potential Cancer Chemopreventives", Steele et al., Cance Epidemiology, Bioarkers and Prevention, vol. 8, May 1999, pp. 467-483.*
Samuel Charache et al., "Effect of Hydroxyurea on the Frequency of Painful Crises in Sickle Cell Anemia", The New England Journal of Medicine, May 18, 1995, vol. 332, No. 20, pp. 1-3.
Richard D. Moore et al., "Cost-Effectiveness of Hydroxyurea in Sickle Cell Anemia", American Journal of Hematology, 64:26-31, 2000, pp. 26-31.
Fact Sheet, "Hydroxyurea in Pediatric Patients with Sickle Cell Disease", Jun. 1998.
James Eckman, M.D., et al., "Sickle Cell Information Center Protocols", Hydroxyurea Therapy Oct. 15, 1997, pp. 1-6.
Allan Platt PA-C et al., "Sicke Cell Research" The Sickle Cell Information Center, Web Update, Aug. 1999, pp. 1-6.
"The Acute Chest Syndrome of Sickle Cell Disease", The New England Journal of Medicine, Jun. 22, 2000, vol. 342, No. 25, pp. 1-3.
"Hydroxyurea and Sickle Cell Crisis", The New England Journal of Medicine, Oct. 12, 1995, vol. 333, No. 15, pp. 1-5.
Elliott P. Vichinsky et al., "Causes and Outcomes of the Acute Chest Syndrome in Sickle Cell Disease", The New England Journal of Medicine, Jun. 22, 2000, vol. 342, No. 25, pp. 1-2.

(Continued)

*Primary Examiner*—Christopher S. F. Low
*Assistant Examiner*—Brian S. Kwon
(74) *Attorney, Agent, or Firm*—Connolly, Bove, Lodge & Hutz, LLP

(57) ABSTRACT

Sickle cell disease is treated by administering a 5-lipoxygenase inhibitor.

7 Claims, 3 Drawing Sheets

OTHER PUBLICATIONS

Graham R. Serjeant, MD, FRCP, "The Geography of Sickle Cell Disease: Opportunities For Understanding Its Diversity", May 1994.

Jeffrey D. Hasday et al., "Anti-Inflammatory Effects of Zileuton in a Subpopulation of Allergic Asthmatics", Am J Respir Crit Care Med, vol. 161, 2000, pp. 1229-1236.

Randy L. Bell et al., "Optimization of the Potency and Duration of Action of N-Hydroxyurea 5-Lipoxygenase Inhibitors", The Journal of Pharmacology and Experimental Therapeutics, vol. 272, No. 2, 1995, pp. 724-731.

"Companies with Ongoing Sicke Cell Research, Treatment Development, or Related Web Sites", The Sickle Cell Information Center, pp. 1-10.

Walid M. Awni et al, "Pharmacokinetics and Pharmacodynamics of Zileuton After Oral Administration of Single and Multiple Dose Regimens of Zileuton 600mg in Healthy Volunteers", Clin Pharmacokinet 29, Suppl 2, 1995, pp. 23-33.

Rene A. Braeckman et al., "The Pharmacokinetics of Zileuton in Healthy Young and Elderly Volunteers", Clin. Pharmacokinet 29, Suppl. 2, 1995, pp. 42-48.

Zileuton (Systemic), Medline plus Health Information, pp. 1-4.

"Hydroxyurea (Systemic)", Medline plus Health Information, pp. 1-6.

The Leukotriene Pathway 1-3, Abbott Laboratories, pp. 1-2, 1-3.

"It's Time to Rethink Your Approach to Treating the Components of Chronic Asthma", Abbott Laboratories, pp. 1-4.

Zyflo Flimtab (zileuton tablets), pp. 1-9.

* cited by examiner

TREATING SICKLE CELL DISEASE

CROSS REFERENCE TO RELATED APPLICATIONS

This application claims priority from provisional U.S. application 60/225,605 filed Aug. 15, 2000, and entitled "Zileuton Treatment for Sickle Cell Disease", disclosure of which is incorporated herein by reference.

STATEMENT REGARDING FEDERALLY SPONSORED RESEARCH OR DEVELOPMENT

This invention was made with support by the Comprehensive Sickle Cell Program under U.S. Government Grant No. P60 HL-38639 awarded by the National Heart, Lung and Blood Institute-National Institute of Health. The U.S. Government has certain non-commercial rights in the invention.

TECHNICAL FIELD

The present invention relates to treating sickle cell disease. In particular, the present invention relates to using a 5-lipoxygenase inhibitor such as zileuton to treat sickle cell disease. According to the present invention, the occurrence of acute chest syndrome and vaso-occlusive crisis associated with sickle cell disease can be reduced

BACKGROUND OF THE INVENTION

Sickle cell anemia is a major public health problem affecting a significant portion of the African-American population. The cause of sickle cell anemia is the substitution of valine for glutamic acid in (beta)-globin. Although this has been known since 1957, it was not until 1995 that for the first time an effective therapy, hydroxyurea, for reducing painful episodes in severely affected adults with sickle cell anemia was clinically shown. Hydroxyurea belongs to a group of medicines referred to as antimetabolites. It appears to increase the flexibility of sickled cells.

Hydroxyurea has been found to decrease the incidence of sickle cell pain crisis and the acute check syndrome. These effects are at least in part related to increase hemoglobin F production by erythroid progenitors from sickle cell patients.

However, it has been observed that hydroxyurea has the tendency to suppress the bone marrow's ability to make red blood cells, white blood cells and platelets.

SUMMARY OF INVENTION

The present invention relates to treating sickle vasocclusive disease and in particular, to using a 5-lipoxygenase inhibitor such as a zileuton or a pharmaceutically acceptable analog thereof or for such purpose. The process of the present invention comprises administering to a patent suffering from sickle cell disease a 5-lipoxygenase inhibitor in an amount effective for treating sickle vasocclusive disease.

According to another aspect of the present invention, the 5-lipoxygenase inhibitor is employed in an amount sufficient to increase the production of hemoglobin F in normal and sickle red blood cells.

A still further aspect of the present invention comprises administering a 5-lipoxygenase inhibitor in an amount sufficient to enhance the expression of gamma globin messenger RNA.

The present invention also relates to administering 5-lipoxygenase inhibitor in an amount sufficient to decrease activated-neutrophil medicated sickle red blood cell retention in lung circulation.

According to the present invention, 5-lipoxygenase inhibitor can also be administered in an amount sufficient to alleviate airway inflammation.

Moreover, the present invention relates to administering 5-lipoxygenase inhibitor in an amount sufficient to decrease accumulation of sickle red blood cells in lung vessels.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modification in various obvious respects, without departing from the invention. Accordingly, the description is to be regarded as illustrative in nature and not as restrictive.

BEST AND VARIOUS MODES FOR CARRYING OUT INVENTION

Figure 1:
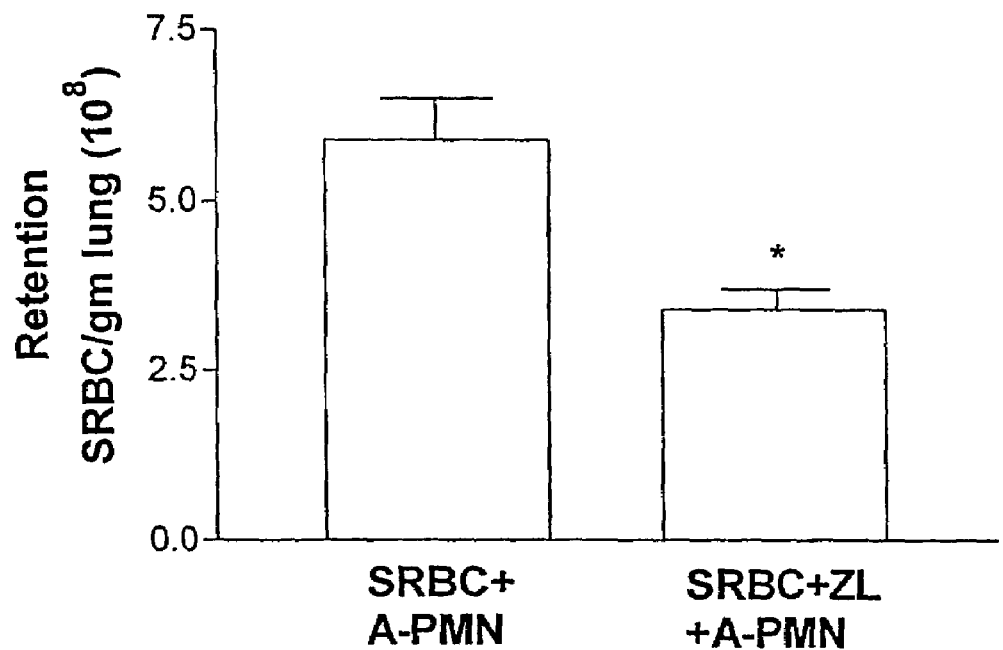
FIG. 1 illustrates that zileuton (ZL) decreases human, activated polymorphonuclear cell (A-PMN, 200,000/ml perfusate) mediated increased SRBC retention in the isolated-perfused lung.

It has been found pursuant to the present invention that 5-lipoxygenase inhibitors can be used to treat sickle vasocclusive disease such as sickle cell anemia, sickle $$B_-^0$$

thalassemia, sickle $$B_+^0$$

thalassemia and sickle-C in humans.

The preferred 5-lipoxygenase inhibitor is zileuton and/or its pharmaceutically acceptable salts thereof. Other 5-lipoxygenase inhibiting compounds are disclosed in U.S. Pat. No. 4,873,259, disclosure of which is incorporated herein by reference.

Pharmaceutically acceptable salts of the compounds of the present invention include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

Zileuton ((±)-1-(1-Benzo[b]thien-2-ylethyl)-1-hydroxyurea), a N-hydroxyurea analog, is a drug currently FDA approved for the treatment of asthma. It is known to exert its effect by blocking the 5-lipoxygenase enzyme. This results in decreased production of substances referred to as leukotrienes (LTs) which promote inflammation in the airways. Airway inflammation is mediated by white blood cells that produce LTs. In human white blood cells, particularly white blood cells referred to as neutrophils and macrophages, $LTB_4$ is the primary LT made. Zileuton blocks the production of $LTB_4$ by the activated neutrophil and macrophage and decreases airway inflammation.

Data generated according to the present invention demonstrates that zileuton enhances the expression of γ globin messenger RNA and increases fetal hemoglobin production in normal and sickle red blood cells. Fetal hemoglobin has been found to decrease pain crisis and the pneumonia-like illness called acute chest syndrome, in sickle cell anemia. Accordingly, zileuton and other 5-lipoxygenase inhibitors can tend to decrease the occurrence of pain crisis and acute chest syndrome. Moreover, it is believed that zileuton would be more effective in treating sickle cell than hydroxyurea, for instance, by decreasing blood vessel blockage by the accumulation of sickle red blood cells and decreasing airway inflammation.

In addition zileuton, in asthmatics, has not been found to suppress the bone marrow's ability to make red blood cells, white blood cells and platelets unlike that previously observed with hydroxyurea.

The following non-limiting examples are presented to illustrate the present invention and demonstrate the effects of zileuton compared to hydroxyurea.

In the following tests, the following materials were used. Zileuton (ZL) was dissolved in 95% ethanol. Hydroxyurea (HU) was dissolved in water.

The Zileuton employed in the human trials below was the commercially available ZYFLO FILMTAB® tablets, orally administered 4 times daily. The tables contain 600 mg. of the active ingredient, zileuton, along with crospovidone, hydroxypropyl cellulose, hydroxypropyl methylcellulose, magnesium stearate, microcrystalline cellulose, pregelatinized starch, propylene glycol, sodium starch glycolate, talc and titanium dioxide (the inactive ingredients).

Isolated perfused lung. Male Sprague-Dawley rats (275–350 g) were anesthetized with Nembutal sodium (25 mg ip), and lungs were removed for extracorporeal perfusion. A tracheostomy was performed that permitted ventilation with a Harvard rodent ventilator (model 683) at 55 breaths/min with a tidal volume of 2.5 ml and 2.0 $cmH_2O$ positive end-expiratory pressure. The inspired gas mixture as 95% air-5% $CO_2$ (room air gas). A median sternotomy was performed, heparin sodium (100 IU) was injected in the right ventricle, and caminulas were placed in the pulmonary artery and left ventricle. Heart, lungs, and mediastinal structures were removed en bloc and placed into a humidified chamber. Lungs were perfused by a Gilson Minipuls 2 peristaltic pump at a constant flow of 0.03 ml·g body $wt^{-1}·min^{-1}$. Lungs were perfused with a physiological salt solution (PSS) containing bovine serum albumin (BSA, 66,000 mol.wt). The PSS-BSA perfusate contained (in mM) 119 NaCl, 4.7 KCl, 1.17 $MgSO_4$, 22.5 $NaHCO_3$, 1.18 $KH_2PO_4$, 3.2 $CaCl_2$, 5.5 glucose, and 4 g/100 ml BSA. PSS-BSA (100 ml) was perfused through the lungs in a nonrecirculating fashion to remove residual blood cells and plasma. The perfusate was then changed to a PSS-BSA perfusate that contained RBCs from individuals homozygous for sickle cell anemia (Hb SS). The perfusate hematocrit was ~10%. Pulmonary arterial pressure ($P_{pa}$) and pulmonary venous ($P_{pv}$) were continuously monitored with Cope pressure transducers (model 041-500-503) and recorded on a Grass polygraph recorder (model 7E). Zone 3 flow conditions (arterial>venous>alveolar pressures) were maintained throughout all experiments.

Blood collection. During steady-state, blood samples (~40 ml) were obtained from normal (Hemoglobin A) human volunteers and from individuals with homozygous sickle cell anemia in the sickle cell clinics at the University of South Alabama. Samples were collected in syringes containing heparin and utilized within 48 hours of collection. Individuals having received blood transfusions within 6 wks were excluded from this study. Sickle cell anemia was documented by hemoglobin electrophoresis in each subject.

RBC isolation and $Cr^{51}$ labeling. Each whole blood sample was centrifuged at 4100 rpm for 10 min followed by the removal of the plasma and buffy coat. Packed RBCs were then mixed at a 1:3 dilution with normal saline and washed ×3. With each wash, the RBC suspension was centrifuged for 10 min at 3000 rpm followed by removal of the supernatant. Following the third wash, packed RBCs were resuspended in PBS (1 ml PBS/1 ml packed RBCs) and incubated with 100 μCi $Cr^{51}$ for 60 min in a shaker water bath at 37° C. Following incubation, the $Cr^{51}$ labeled RBCs were washed ×1 with normal saline and resuspended in PSS-BSA to obtain a hematocrit of ~10%.

Neutrophil (PMN) isolations. Heparinized whole blood (20 ml) from individuals with homozygous sickle cell anemia was diluted 1:1 with normal saline. Dextran 500 was added to the 1:1 mix at ¼ the volume of the 1:1 mix. This was allowed to incubate for 45 min at 37° C. The supernatant (contains PMNs) was aspirated into a 50 ml centrifuge tube and underlayered with 10 ml histopague 1077. This was centrifuged at 1250 rpm for 30 min. The supernatant is aspirated and discarded leaving the PMN pellet. Sterile $H_2O$, 3 ml, is added to the PMN pellet and agitated for 3 sec to lyse any residual RBCs. Phosphate buffered saline, 45 ml, is added immediately thereafter to stop the reaction. This is centrifuged at 1250 rpm for 10 min. The supernatant is aspirated and discarded. This process of RBC lysis followed by PBS is repeated until the PMN pellet is without visual evidence of RBC contamination. The PMN pellet is suspended in 1 ml of sterile Hank's balanced salt solution. A total PMN count is obtained using the Cell-DYN 900 Coulter Counter. PMN viability is 95–99% as assessed using trypan blue.

Heat Inactivation of Neutrophils. Purified PMNs suspended in 1 mL of sterile Hank's balanced salt solution, pH 7.4 is transferred to a siliconized glass tube and placed in a 48° C. water bath with constant agitation for 10 min. [25,26] Aliquots of the heat-treated PMN suspension are immediately added to a 10% sickle RBC suspension to obtain a final PMN concentration of ~200,000/mL of perfusate.

RBC Retention. Cell counts of the $Cr^{51}$ labeled RBC suspension are obtained in a Cell-DYN 900 Coulter Counter. The specific activity of the $Cr^{51}$ labeled RBC perfusate is calculated flowing gamma counts at 162–176 Kev for one minute and expressed as cpm/RBC. The isolated lung is then perfused with the $Cr^{51}$ labeled RBC perfusate for 30 minutes. Following this, the lung is washed with 100 ml of RBC-free PSS-BSA under identical hemodynamic conditions. Perfusion is stopped, and the lung is dissected into lobes and weighed. Each lobe is gamma counter for one minute. Retention (R) is calculated as:

$R$=SPECIFIC ACTIVITY OF LUNG/SPECIFIC ACTIVITY OF PERFUSATE $R$=cpm/GRAM OF LUNG/cpm/RBC $R$=RETAINED RBC/GRAM OF LUNG In the isolated perfused lung, the increased retention of SRBCs can occur from increased adhesion to vascular endothelium or secondary to mechanical obstruction. Thus hereinbelow the number of retained SRBCs per gram lung is referred to as a retention/adherence.

Isolated Perfused Lung Protocol. Using the isolated rat lung preparation, 48 lungs were perfused with 10% hematocrit SRBC suspension +A-PMN (200,000/ml of perfusate) and ventilated with a 21% $O_2$-5% $CO_2$ gas mixture. Paired SRBC+PMN samples were utilized in each study. Paired SRBC+PMN samples were used in order to minimize patient to patient variability as well as within patient variability relative to time. The activation of PMNs was achieved by the addition of PMA (20 ng/ml) to the perfusate reservoir at the initiation of lung perfusion in all experiments. Lungs were perfused in a recirculating fashion under constant flow conditions for 30 minutes and the retention/adherence of SRBC was determined as previously described. The following comparisons of SRBC retention relative to PMN activation were made: 1) SRBC+A-PMN control vs SRBC+ZL (2.5 µM pretreated A-PMN (n=10 each); and 2) SRBC+A-PMN control vs SRBC+HU (50 µM) pretreated A-PMN (n=6 each) or HU (100 µM) pretreated A-PMN (n=5 each) or HU (1000 µM) pretreated A-PMN (n=5 each). In all tests, PMNs were incubated with either the diluents of ZL and HU or ZL and HU, for 30 minutes in the test tube prior to being added to the perfusate reservoir and activation with PMA.

BFU-E Colony Growth. Mononuclear cells were isolated from the peripheral blood of each patient studied by density gradient centrifugation using Histapaque-1077 (Sigma). Erythroid progenitors were obtained in methylcellulose culture. ZL was added on day 0 at 25, 50, 75, or 100 µM concentrations for 13–14 days at which time the number of BFU-E colonies were counted on an inverted microscope and harvested for hemoglobin determinations.

Hemoglobin F determination. The erythroid progenitors were collected, washed in PBS then lysed at room temperature in 200 µl of water. The supernatant was split into two tubes, one for total hemoglobin determination and one for hemoglobin F determination. In brief, IgG (10 µl), 1.2 N NaOH (7 µl) and saturated $(NH_4)_2SO_4$ (70 µl) were added to the hemoglobin F sample. The denatured hemoglobin was pelleted and the supernatant containing hemoglobin F was mixed with 500 µl of tetramethyl benzidine and 500 µl of $H_2O_2$ at room temperature then quantitated on a spectrophotometer at 600 nm. The percentage of fetal hemoglobin to total hemoglobin was determined.

Cell Culture. K562 cells were grown in suspension cultures in RPMI-1640 containing 10% fetal bovine serum, penicillin (100 U/ml) and streptomycin (0.1 mg/ml in a humidified incubator at 37° C. in a 5%$CO_2$/95% air atmosphere. The following experimental conditions were analyzed in triplicate with $2 \times 10^6$ cells per well: an untreated control, ZL dissolved in 0.1% dimethylsulfoximide (DMSO) at final concentrations of 20, 40, 50, 75 or 100 mM, HU at 50, 75 or 100 mM and two positive controls hemin (50 mM) and sodium butyrate (NB) 2 mM. The K562 cells were induced for 72 hours then RNA isolated for further analysis. Cell viability was completed by 2% trypan blue exclusion at timnes 0 and 72 hours.

RNA Isolation. RNA was isolated using RNA Stat-60 (TEL-TEST "B", Inc., Friendswood, Tex.) according to the manufacturer's instructions. In brief, cell pellets will be suspended in RNA Stat-60 (1 ml) and chloroform (200 µl), and the RNA extracted and precipitated with isopropanol.

RNase Protection Analysis. MRNA levels will be quantitated by RNase protection assay (RPA) with probes designed to yield protected fragments for human γ (Huγ)and the internal control glyceraldehydes-3-phosphate dehydrogenase (GAPD). Huγ mRNA levels were normalized to that of GAPD and compared to the untreated K562 cells. (Zar: Statistical Analysis, Englewood)

Statistics. All results are presented as means±SE. Statistical analyses were performed using the unpaired Student's t test and one-way analysis of variance (ANOVA). Tukey's test and Dunnett's was used for multiple comparisons when ANOVA indicated statically significant differences between or within groups. Differences were considered to be significant when $p<0.005$.

The following results were obtained.

Zileuton Decreased SRBC Retention/Adherence more Effectively than Hydroxyurea.

Figure 2:
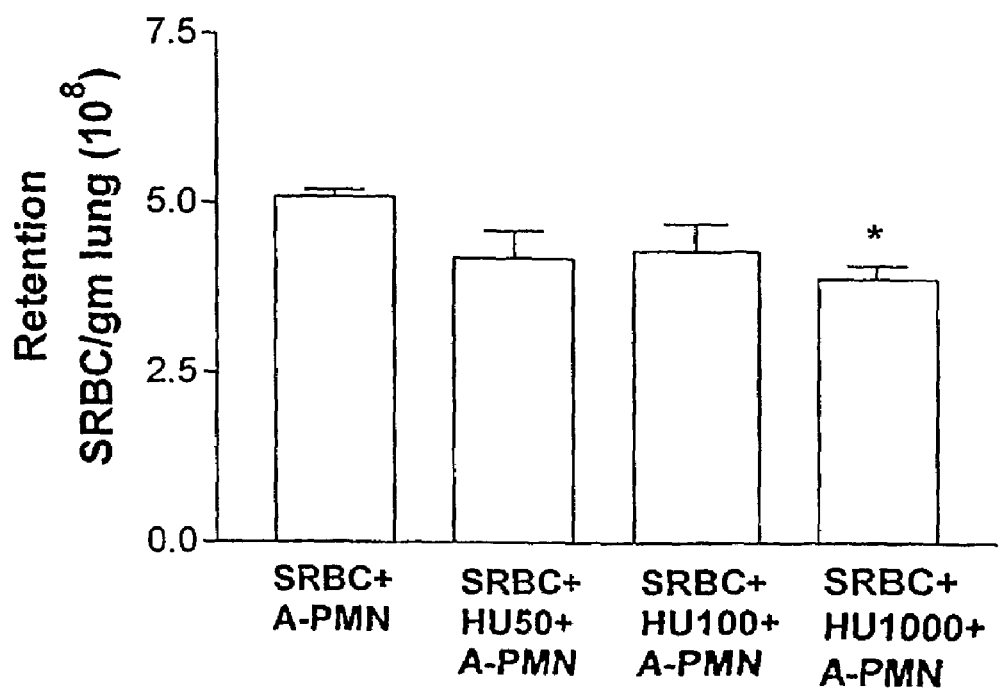
FIG. 2 illustrates that Hydroxyurea (HU), in a supraphar-mocologic concentration, decreases A-PMN mediated increased SRBC retention in the isolated-perfused lung.

The ability of HU to decrease SRBC retention/adherence as compared to ZL in the isolated rat lung was tested. When comparing SRBC retention/adherence in lungs of SRBC+A-PMN controls (ethanol diluent) to lungs perfused with SRBC+ZL pretreated A-PMNs, the number of retained SRBCs were significantly different (p=0.0002) at $5.9 \pm 0.6 \times 10^8$, respectively. ZL pretreatment of A-PMNs resulted in a ~42% decrease in SRBC retention/adherence (FIG. 1). In contrast, no significant differences were seen when comparing retention/adherence in the SRBC+A-PMN controls ($H_2O$ diluent) for the HU studies. In HU controls, SRBC retention/adherences were $4.9 \pm 0.2 \times 10^8$ (50 µM), $5.4 \pm 0.3 \times 10^8$ (100 µM), and $5.0 \pm 0.2 \times 10^8$ (1000 µM) SRBC/gram of lung. This mean±SEM SRBC retention/adherence for controls was $5.1 \pm 0.1 \times 10^8$ SRBC/gram of lung. SRBC retention/adherence in the SRBC+HU pretreated A-PMN lungs at 50, 100 and 1000 µM were $4.2 \pm 0.4$, $4.3 \pm 0.4$, and $3.9 \pm 0.2 \times 10^8$ SRBC/gram of lung, respectively. As compared with control, a significant (p<0.05) decrease of ~25% in retained SRBCs was seen in lungs whose PMNs were pretreated with HU, 1000 µM, prior to activation (FIG. 2).

Zileuton Induces Fetal Hemoglobin in Primary Erythroid Progenitors.

The capability of ZL to induce hemoglobin F in primary erythroid progenitors, grown from peripheral blood mononuclear cells (MNC) was analyzed. BFU-E colonies were grown in methylcellulose cultures supplemented with erthyopoietin and interleukin-3 and ZL at concentration from 0 to 100 µM. Three patients homozygous for hemoglobin S (Hb SS) were analyzed with triplicate experiments. The average BFU-E colony number was 123.2±18.6 without ZL compared to 10.6±2.0 at 100 µM concentrations, p<0.05 (Table 1). In contrast to the decline in BFU-E colonies, hemoglobin F levels increased from 3.4±1.7 to 15.9±1.4 (p<0.05), thus demonstrating the ability of ZL to induce hemoglobin F production in primary erythroid progenitors. All pair-wise comparisons for BFU-E and hemoglobin F between 0µ and other concentrations (25, 50, 75 and 100 µM) were significant at p<0.05. The correlation coefficient between the number of BFU-E colonies or percent hemoglobin F and different levels of ZL is −0.90 and +0.79, respectively (p<0.05). These results are comparable to data previously published on HU. (See Yang et al., BFU-E colony growth in response to hydroxyurea: correlation between in vitro and in vivo fetal hemoglobin induction. Am J Hematol. 1997; 56:252–258). A dose dependent 11.7-fold decrease (p<0.05) in BFU-E colony number was observed at the 0 versus 100 μM ZL concentration as compared to a 21.3-fold decrease (p<0.05) for HU in BFU-E colonies grown from Hb SS patients (Table 2). HU either was more efficient in inhibiting BFU-E colony growth or alternatively the baseline number of colonies on an average was higher for the Hb SS patients in the HU cohort. Despite less change in the number of BFU-E growth with ZL, a 4.8-fold increase in hemoglobin F compared to a 3.8-fold increase in HU suggesting comparable γ gene induction for both drugs was observed.

Figure 3A:
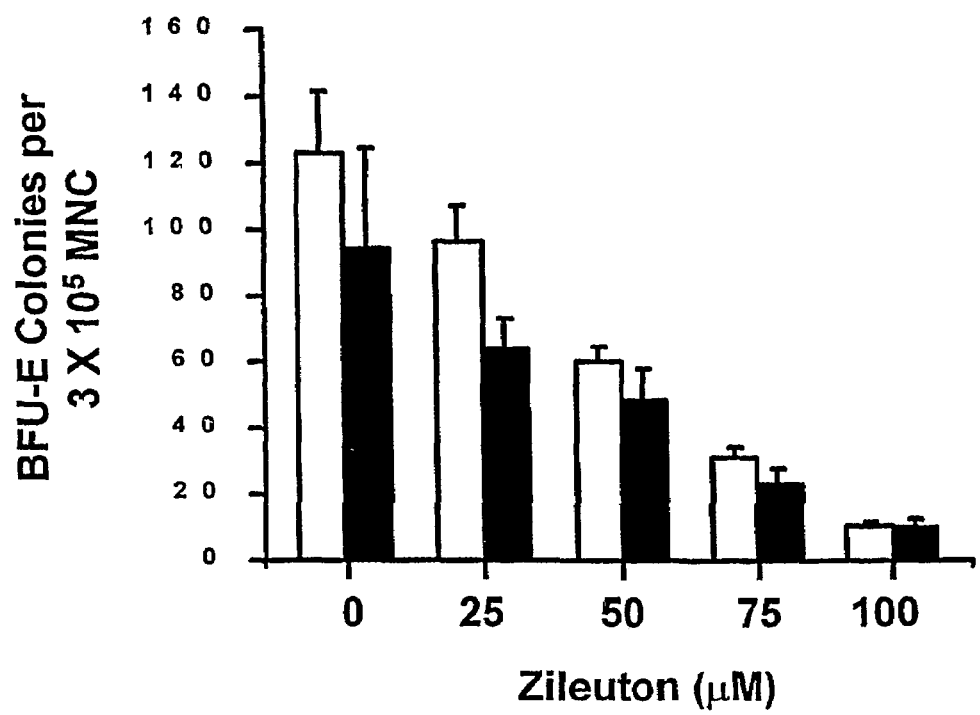
FIG. 3A-B show BFU-E colony growth and fetal hemoglobin production in the presence of zileuton for Hb SS and normal patients in methylcellulose culture.
Figure 3B:
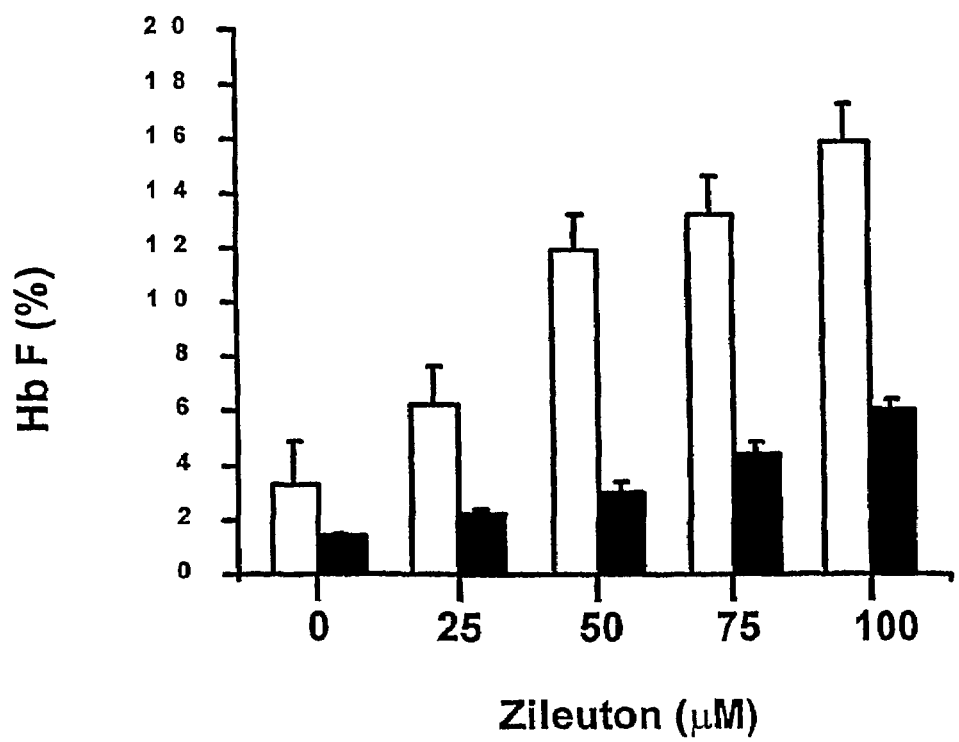

The cytotoxic effect of HU as been proposed as a basic mechanism involved in hemoglobin F induction. In the absence of this characteristic for ZL, whether γ gene expression would be, induced in erythroid progenitors obtained from normal donors was tested. Utilizing the same protocol, BFU-E colonies from normal donors wee analyzed in the presence of ZL at 0 to 100 μM concentrations. In normal erythroid progenitors, a decrease in BFU-E colony number from 94±30.6 to 10.1±2.4 (FIG. 3A) and an increase in hemoglobin F from 1.4±0.05% to 6.0± (FIG. 3B) was observed. This pattern was similar to that obtained for Hb SS progenitors. Of note is the lower average BFU-E colony number for hemoglobin A progenitors as compared with hemoglobin S. This probably reflects the absence of hemolysis and increased RBC production in normals as compared to sickle cell patients. This represents a 9.3-fold decrease and a 4.3-fold increase in BFU-E and hemoglobin F, respectively. Pair-wise comparisons of BFU-E colony growth for normal samples revealed significant decreases between ZL, 0 μM and the 50, 75 and 100 μM concentrations (p<0.05). In contrast, hemoglobin F levels were significantly increased at ZL concentrations of 50, 75 and 100 μM as compared to ZL, 0 μM (p<0.05).

Zileuton Augments γ Gene mRNA Levels in vitro in K562 Cells.

Figure 4A:
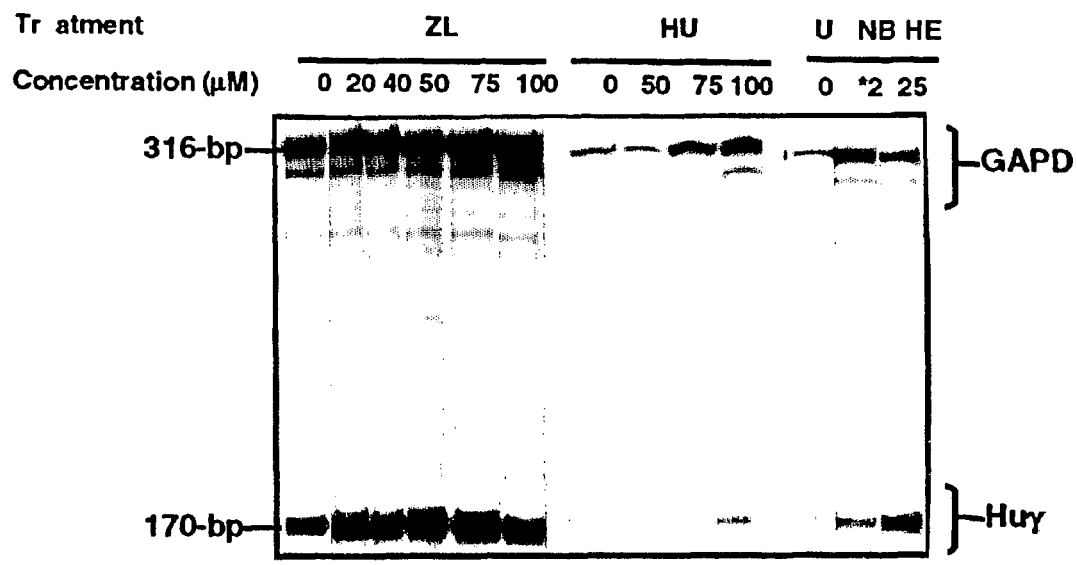
FIG. 4A-B show $\gamma$ gene induction by zileuton in K562 cells.
Figure 4B:
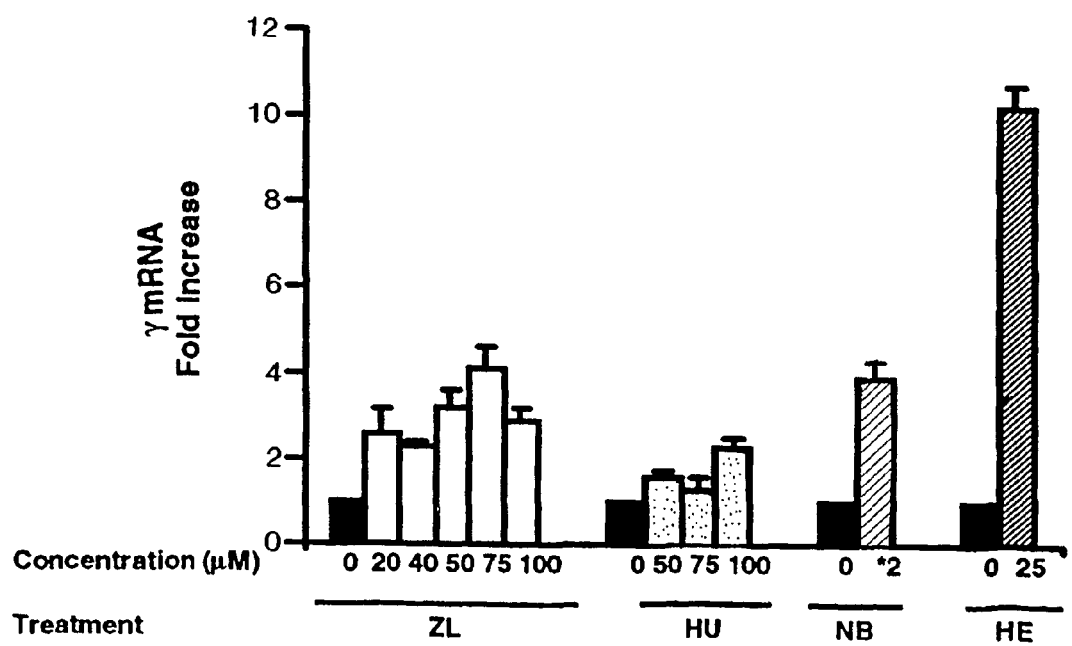

Several pharmacological hemoglobin F inducers such as HU, 5-azacytidine, erythropoietin, didox, and butyrate alter γ gene expression in culture. The induction of γ gene activity in culture is a good indicator of potential clinical usefulness. Therefore the capability of ZL to induce γ gene activity at the mRNA level was tested. K562 cells were cultured in ZL from 0 to 100 μM or HU (50μ to 100 μM) for 48 hours. Total cellular RNA was analyzed by RPA for γ mRNA levels. An increase in γ mRNA for ZL at 20 μM with a maximal response at 75 μM (FIG. 4A) was observed. The level of γ gene mRNA synthesis was quantitated relative to the internal control, CAPD. As shown in FIG. 4B, there was a maximal 4.1-fold increase in γ mRNA at ZL 75 μM as compared to a 2.7-fold increase for HU at 100 μM (p<0.05). Of note is the observation that ZL increased γ mRNA 2.6 fold at the 20 μM concentration demonstrating comparable induction to 100 μM HU (FIG. 4B). This suggests ZL is a more potent inducer of γ gene activity than HU in the K562 cell. K562 cell viability was decreased 10% when measured using trypan blue exclusion at 75 μM and 100 μM concentrations for both ZL and HU. The level of γ gene induction was 3.9 fold and 10-fold for the positive controls NB and hemin, respectively.

The above results show the following: 1) ZL decreases SRBC retention/adherence mediated by activated-PMN in the isolated-perfused rat lung; 2) to a lesser extent than seen with ZL (2.5 μM), HU decreases SRBC retention/adherence in a suprapharmocologic concentration (1 μM); 3) ZL induces hemoglobin F in primary erythroid progenitors comparable to that observed with HU; and 4) in K562 cells, ZL is more potent than HU in γ gene mRNA induction.

PMN activation is required to enhance SRBC retention/adherence in the isolated lung perfused with SRBC+PMNs. The above tests further support that ZL pretreatment of PMNs prior to activation with PMA, decreases SRBC retention ~42% as compared to activated-PMN controls. The mechanism of attenuation for activated-PMN effect(s) on enhanced SRBC retention/adherence is at least in part dependent on 5-LO enzyme inhibition and decreased $LTB_4$ production.

Similar to ZL, pretreatment of PMNs with HU in a suprapharmocologic concentration (1000 μM), attenuated activated-PMN mediated SRBC retention/adherence ~25%. Lower concentrations of HU (50 and 100 μM) did not attenuate activated-PMN mediated enhanced SRBC retention/adherence. Hillery, et al., (Hydroxyurea therapy decreases the in vitro adhesion of sickle erythrocytes to thrombospondin and laminin. Br J Haematol. 2000;109(2): 322–327) have shown that SRBCs from patients on HU therapy demonstrated decreased adhesivity to thrombospondin and laminin in vitro. Saleh, et al., (Cytokines and soluble adhesion molecules in sickle cell anemia patients during hydroxyurea therapy. Acta Haematol. 1998; 100(1):26–31) found that steady state sVCAM-1 levels are increased in SCD and decreased significantly during HU therapy over 5 months as did PMN activity. These observations suggest HU decreases SRBC adhesion to vascular endothelium by down regulating endothelial cell VCAM-1 and/or through yet unexplained effects of activated PMNs. Why little or no effect of HU on attenuating SRBC retention/adherence was seen in these tests is not clear.

The above data clearly demonstrates a greater ability of ZL to induce γ gene activity at the transcriptional level when compared HU at a given concentration. An in vitro cell culture system was used to analyze the effects of ZL on BFU-E colony growth. The above initial studies establish a dose response curve for ZL versus BFU-E number, similar to that previously shown for HU. A consistent decrease in BFU-E colony number as the concentration of ZL increased to 100 μM, which is pharmacologically achievable was observed. This data suggest a role for cytotoxicity in the mechanism of action for hemoglobin F induction by ZL.

Unique to ZL as compared to HU is an anti-inflammatory effect(s). The above tests support ZL as a potential new and superior agent to HU with dual effectiveness as an antisickling and anti-inflammatory agent that can be used in the prevention and treatment of sickle vasocclusive crisis and acute chest syndrome.

The 5-lipoxygenase inhibitor can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The pharmaceutically acceptable carriers described herein, for example, vehicles, adjuvants, excipients, or diluents, are well known to those who are skilled in the art. Typically, the pharmaceutically acceptable-carrier is chemically inert to the active compounds and has no detrimental side effects or toxicity under the conditions of use. The pharmaceutically acceptable carriers can include polymers and polymer matrices.

The 5-lipoxygenase inhibitor can be administered by any conventional method available for use in conjunction with pharmaceuticals.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (g) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5–95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The 5-lipoxygenase inhibitors can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238–250 (1982) and *ASHP Handbook on Injectable Drugs*, Toissel, 4th ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Suitable pharmaceutical carriers are described in Remington's Pharmaceutical Sciences, Mack Publishing Company, a standard reference text in this field.

The dose administered in the context of the present invention should be sufficient to effect the therapeutic response over a reasonable time frame. One skilled in the art will recognize that dosage will depend upon a variety of factors including a condition of the human patient and the body weight.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the 5-lipoxygenase inhibitors according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the 5-lipoxygenase inhibitors can be administered in the form of nose drops, or metered dose and a nasal or buccal inhaler. The drug is delivered from a nasal solution as a fine mist or from a powder as an aerosol.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

TABLE 1

Effects of zileuton on BFU-E colony growth and fetal hemoglobin production in primary erythroid cultures.

| | Zileuton Concentrations (µM) | | | | | | | | | |
|---|---|---|---|---|---|---|---|---|---|---|
| | 0 | | 25 | | 50 | | 75 | | 100 | |
| Patient No. | BFU-E | HbF | BFU-E | HbF | BFU-E | HbF | BFU-E | HbF | BFU-E | HbF |
| 1 | 87 | 2 | 61 | 4 | 47 | 7 | 27 | 11 | 12 | 14 |
| 2 | 135 | 7 | 91 | 11 | 72 | 14 | 43 | 18 | 7 | 21 |
| 3 | 148 | 2 | 137 | 3 | 62 | 6 | 23 | 11 | 13 | 13 |

TABLE 1-continued

Effects of zileuton on BFU-E colony growth and fetal hemoglobin production in primary erythroid cultures.

| | Zileuton Concentrations (μM) | | | | | | | | | |
|---|---|---|---|---|---|---|---|---|---|---|
| | 0 | | 25 | | 50 | | 75 | | 100 | |
| Patient No. | BFU-E | HbF | BFU-E | HbF | BFU-E | HbF | BFU-E | HbF | BFU-E | HbF |
| Mean + SEM | 123.2 ± 9.4 | 3.3 ± 1.6 | 96.4 ± 11.1 | 6.2 ± 1.4 | 60.4 ± 4.3 | 11.9 ± 1.3 | 31.1 ± 3.2 | 13.2 ± 1.4 | 10.5 ± 1.3 | 15.9 ± 1.4 |
| P value | — | — | <0.05 | <0.05 | <0.05 | <0.05 | <0.05 | <0.05 | <0.05 | <0.05 |

BFU-E = burst forming unit-erythroid,
HbF = fetal hemoglobin in percent (%)
HbSS = sickle cell patient.
*P value represent a comparison to 0 μM zileuton concentration in the number of BFU-E colonies and in the fetal hemoglobin level.

TABLE 2

Comparison between hydroxyurea and zileuton for change in BFU-E colony and HbF levels in primary erythroid progenitors from sickle cell patients.

| | BFU-E | | | P value | HbF | | | P value |
|---|---|---|---|---|---|---|---|---|
| | | | Difference | | | | Difference | |
| Concentration (μM) | 0 | 100 | | | 0 | 100 | | |
| ZL | 123.2 | 10.5 | 112.6 ± 19.1 | <0.05 | 3.3 | 15.9 | 12.6 ± 1.1 | <0.05 |
| HU | 153.7 | 7.2 | 146.4 ± 9.1 | <0.05 | 5.1 | 19.4 | 14.4 ± 1.5 | <0.05 |

ZL = zileuton,
HU = hydroxyurea,
BFU-E = burst forming unit-erythroid,
HbF = fetal hemoglobin in percent (%).

What is claimed:

1. A method for treating sickle vasocclusive disease which comprises administering to a patient in need thereof zileuton or a pharmaceutically acceptable salt thereof in an amount effective for treating sickle vasocclusive disease.

2. The method of claim 1 wherein the sickle vasocclusive disease is sickle cell anemia.

3. The method of claim 1 wherein the sickle vasocclusive disease is sickle thalassemia.

4. A method of treating sickle vasocclusive disease which comprises administering to a patient in need thereof zileuton or a pharmaceutically acceptable salt thereof in an amount sufficient to increase the production of fetal hemoglobin in normal and sickle red blood cells.

5. A method of treating sickle vasocclusive disease which comprises administering to a patient in need thereof zileuton or a pharmaceutically acceptable salt thereof in an amount sufficient to enhance the expression of gamma globin messenger RNA.

6. A method of treating sickle vasocclusive disease which comprises administering to a patient thereof zileuton or a pharmaceutically acceptable salt thereof in an amount sufficient to decrease activated-neutrophil mediated sickle red blood cell retention in lung circulation.

7. The method of claim 1 wherein acute chest syndrome and pain crisis in sickle vasocclusive disease is treated.

* * * * *